(12) United States Patent
Politis et al.

(10) Patent No.: US 12,364,813 B2
(45) Date of Patent: Jul. 22, 2025

(54) PRESSURE INDICATOR FOR MEDICAMENT DELIVERY DEVICE

(71) Applicant: Becton, Dickinson and Company, Franklin Lakes, NJ (US)

(72) Inventors: Victor Politis, Natick, MA (US); John Perez, East Boston, MA (US); Jacob Wainer, Medford, MA (US); Alex Chaves, Tyngsboro, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 229 days.

(21) Appl. No.: 18/115,083

(22) Filed: Feb. 28, 2023

(65) Prior Publication Data

US 2023/0201458 A1 Jun. 29, 2023

Related U.S. Application Data

(62) Division of application No. 16/777,453, filed on Jan. 30, 2020, now Pat. No. 11,596,739.

(60) Provisional application No. 62/799,420, filed on Jan. 31, 2019.

(51) Int. Cl.
| | |
|---|---|
| *A61M 5/168* | (2006.01) |
| *A61M 5/145* | (2006.01) |
| *A61M 5/172* | (2006.01) |
| *A61M 5/34* | (2006.01) |
| *A61M 5/48* | (2006.01) |
| *A61M 5/14* | (2006.01) |

(52) U.S. Cl.
CPC ........ *A61M 5/16854* (2013.01); *A61M 5/145* (2013.01); *A61M 5/16859* (2013.01); *A61M 5/172* (2013.01); *A61M 5/343* (2013.01); *A61M 5/484* (2013.01); *A61M 5/486* (2013.01); *A61M 2005/1401* (2013.01)

(58) Field of Classification Search
CPC .. A61M 5/486; A61M 5/484; A61M 5/16854; A61M 5/16859
See application file for complete search history.

(56) References Cited

U.S. PATENT DOCUMENTS

| | | | |
|---|---|---|---|
| 5,039,279 | A | 8/1991 | Natwick et al. |
| 5,059,182 | A | 10/1991 | Laing |
| 6,358,225 | B1 | 3/2002 | Butterfield |
| 8,617,110 | B2 | 12/2013 | Moberg et al. |

(Continued)

FOREIGN PATENT DOCUMENTS

| | | |
|---|---|---|
| CN | 205658923 U | 10/2016 |
| CN | 212522592 U | 2/2021 |

(Continued)

*Primary Examiner* — Jenna Zhang
(74) *Attorney, Agent, or Firm* — Dickinson Wright PLLC

(57) ABSTRACT

A medicament delivery device having a reservoir for holding a medicament, a pressurizing system that dispenses the medicament from the reservoir when operating, a hollow cannula for insertion into a patient, and a fluid delivery path disposed between the pressurizing system and the hollow cannula and communicating the medicament therebetween. The medicament delivery device also has a pressure sensor external to the pressurizing system, sensing a back pressure in the fluid delivery path, and providing an indication when the back pressure drops below a predetermined threshold after the pressurizing system ceases operation.

6 Claims, 15 Drawing Sheets

(56) References Cited

U.S. PATENT DOCUMENTS

| | | | |
|---|---|---|---|
| 2008/0015406 A1* | 1/2008 | Dlugos | A61M 5/14586 |
| | | | 600/37 |
| 2012/0046546 A1* | 2/2012 | Strobl | A61M 5/16854 |
| | | | 600/431 |
| 2012/0123194 A1* | 5/2012 | Beckman | A61M 25/1018 |
| | | | 600/37 |
| 2014/0350517 A1* | 11/2014 | Dominguez | A61M 5/31501 |
| | | | 604/218 |
| 2015/0314074 A1* | 11/2015 | Howlett | A61M 5/31595 |
| | | | 604/222 |
| 2016/0030683 A1* | 2/2016 | Taylor | A61M 5/345 |
| | | | 604/151 |

FOREIGN PATENT DOCUMENTS

| | | | |
|---|---|---|---|
| JP | 2005527334 A | 9/2005 | |
| JP | 2006503600 A | 2/2006 | |
| JP | 2013505794 A | 3/2013 | |
| JP | 2014500778 A | 1/2014 | |
| JP | 2016512144 A | 4/2016 | |

* cited by examiner

MINIMED LUER-LOCK

PRESSURE INDICATOR FOR MEDICAMENT DELIVERY DEVICE

CROSS-REFERENCE TO RELATED APPLICATION

This application is a divisional of U.S. patent application Ser. No. 16/777,453, filed on Jan. 30, 2020, which claims priority under 35 USC § 119(e) from U.S. provisional patent application Ser. No. 62/799,420, filed on Jan. 31, 2019, the disclosure of which is incorporated herein by reference in its entirety.

FIELD OF THE INVENTION

The present invention relates to medical devices, and more particularly, to medical devices with a cannula and a pressurizing system.

BACKGROUND OF THE INVENTION

After a medicament pressurizing system of a medicament delivery device ceases operation, pressure in the fluid delivery path of the device does not immediately drop to zero. Until the pressure in the fluid delivery path drops below a certain threshold, medicament delivery continues. For example, during insulin infusion when using a pump 14 (FIG. 1), residual pressure within the system may build up and be present after the pump 14 stops operating. Premature removal or disconnection (see FIG. 1) of an insulin infusion set or fluid connector 10 from a base or infusion site 80 inserted in a patient may lead to insulin evacuating the fluid connector 10 (see FIG. 2) after removal of the set. In such a situation, therefore the user will not receive all of the intended dosage.

Pressure required to deliver 1 unit of insulin is roughly equal to 0.7 psi. Therefore a low residual pressure in the infusion set post removal or disconnection could mean significant loss in therapy. For example, a 1-unit loss out of a 10-unit bolus results in delivery of only 90% of intended insulin dose. Improvements are desirable.

SUMMARY OF EMBODIMENTS OF THE INVENTION

Accordingly, it is an aspect of the present invention to provide a medicament delivery device having an indicator to let a user know when it is safe to remove or disconnect the medicament delivery device.

The foregoing and/or other aspects of the present invention are achieved by providing a medicament delivery device having a reservoir for holding a medicament, a pressurizing system that dispenses the medicament from the reservoir when operating, a hollow cannula for insertion into a patient, and a fluid delivery path disposed between the pressurizing system and the hollow cannula and communicating the medicament therebetween. The medicament delivery device also has a pressure sensor external to the pressurizing system, sensing a back pressure in the fluid delivery path, and providing an indication when the back pressure drops below a predetermined threshold after the pressurizing system ceases operation.

The foregoing and/or other aspects of the present invention are also achieved by providing a medicament delivery pen having a reservoir for holding a medicament, a pressurizing system that dispenses the medicament from the reservoir when operating; and a needle hub housing a hollow cannula, the hollow cannula having a distal end for insertion into a patient. The medicament delivery pen also has a fluid delivery path disposed between the pressurizing system and the distal end of the hollow cannula and communicating the medicament therebetween, and a pressure sensor external to the pressurizing system and disposed in the hub, sensing a back pressure in the fluid delivery path, and providing an indication when the back pressure drops below a predetermined threshold after the pressurizing system ceases operation.

The foregoing and/or other aspects of the present invention are also achieved by providing medicament delivery syringe having a reservoir for holding a medicament, a pressurizing system that dispenses the medicament from the reservoir when operating, and a needle hub housing a hollow cannula, the hollow cannula having a distal end for insertion into a patient. The medicament delivery syringe also has a fluid delivery path disposed between the pressurizing system and the distal end of the hollow cannula and communicating the medicament therebetween, and a pressure sensor external to the pressurizing system and disposed in the hub, sensing a back pressure in the fluid delivery path, and providing an indication when the back pressure drops below a predetermined threshold after the pressurizing system ceases operation.

Additional and/or other aspects and advantages of the present invention will be set forth in the description that follows, or will be apparent from the description, or may be learned by practice of the invention.

BRIEF DESCRIPTION OF THE DRAWINGS

Aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
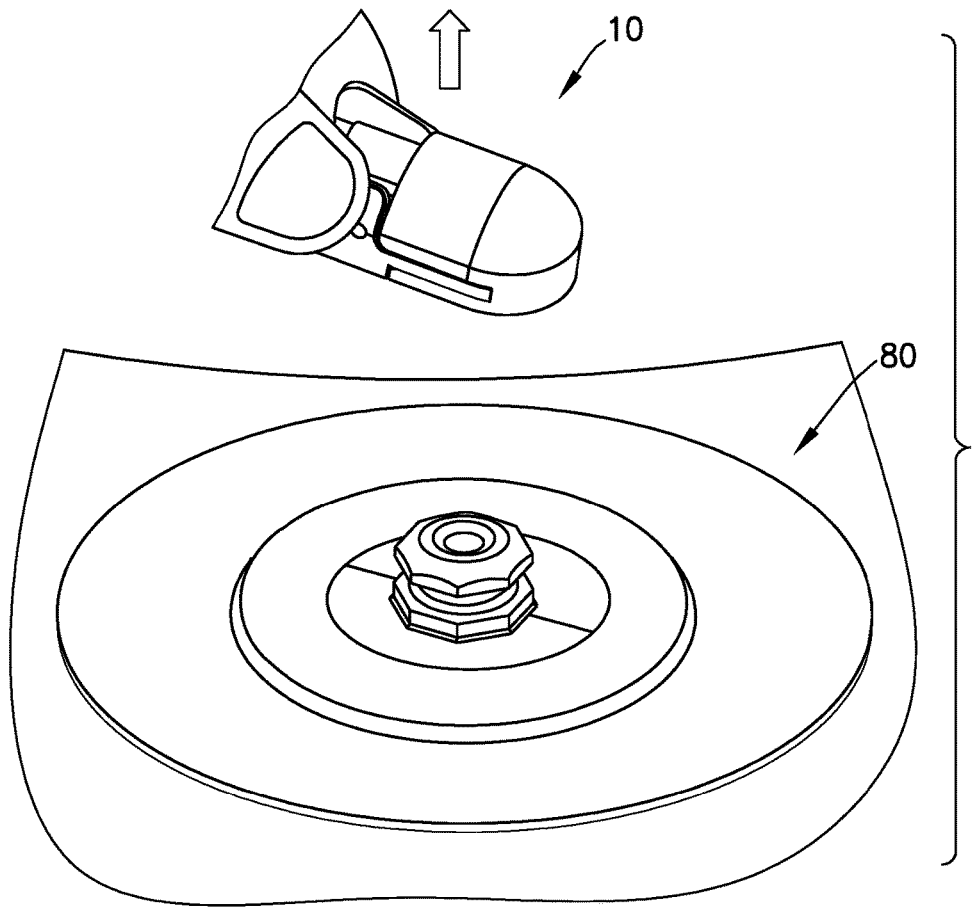
FIG. 1 illustrates removal or disconnection of a medicament infusion fluid connector.
Figure 2:
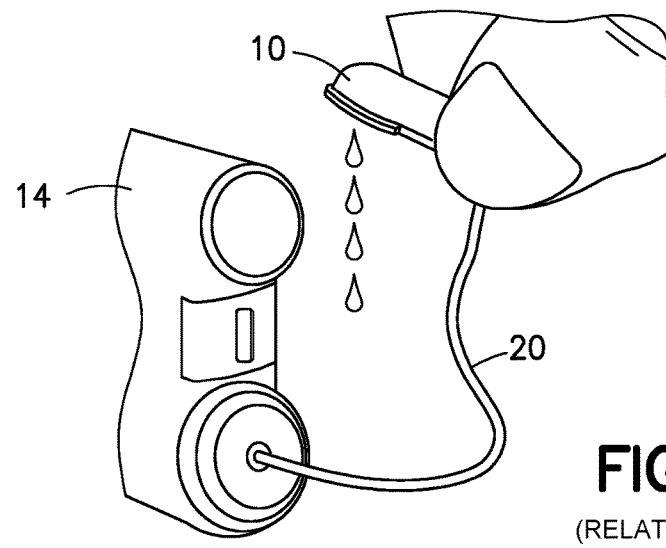
FIG. 2 illustrates evacuation of medicament from the fluid connector of FIG. 1.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive; features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled"" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Figure 3:
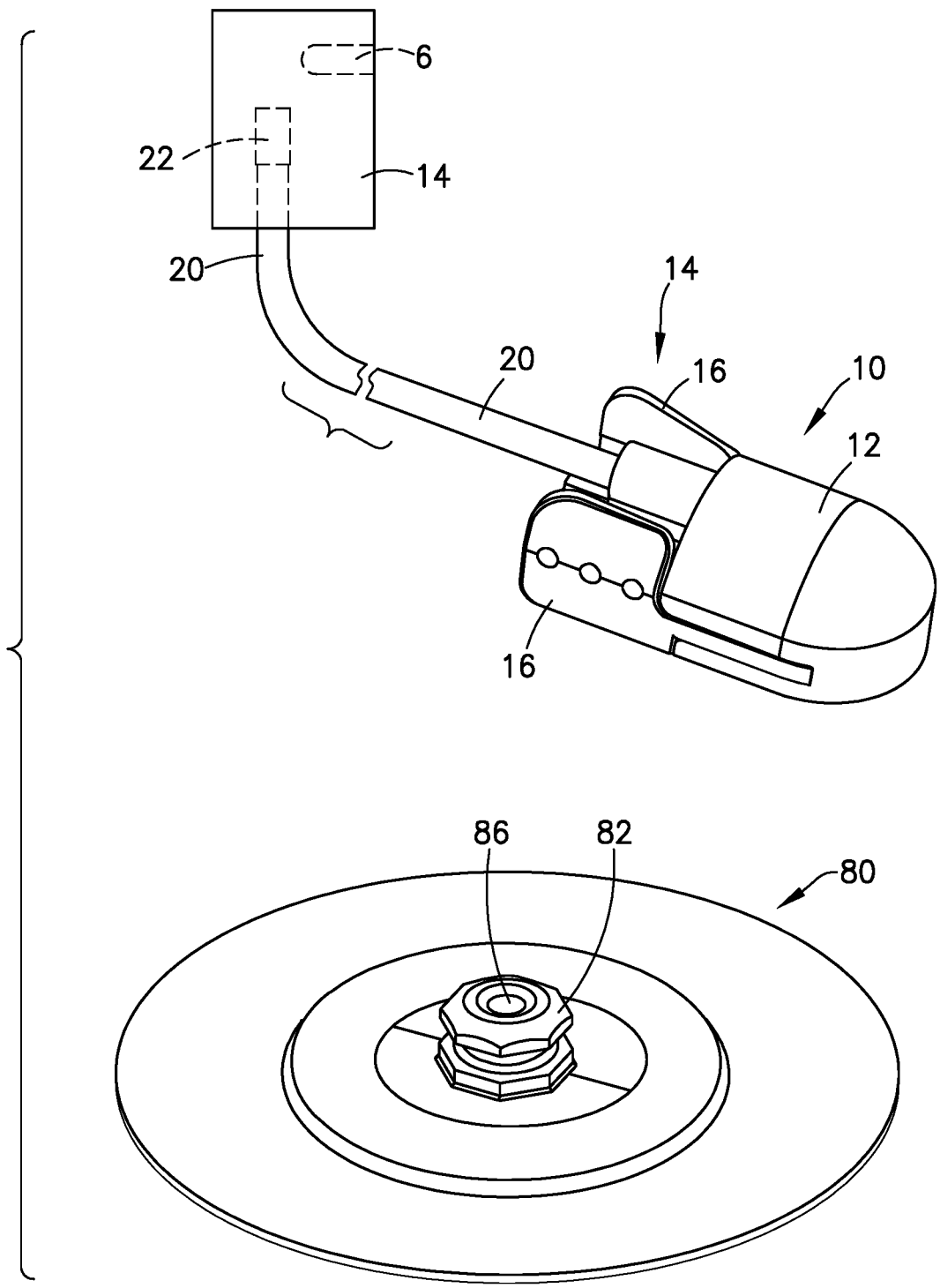
FIGS. 3-5 are various views of a related art fluid connector and an associated base.
Figure 4:
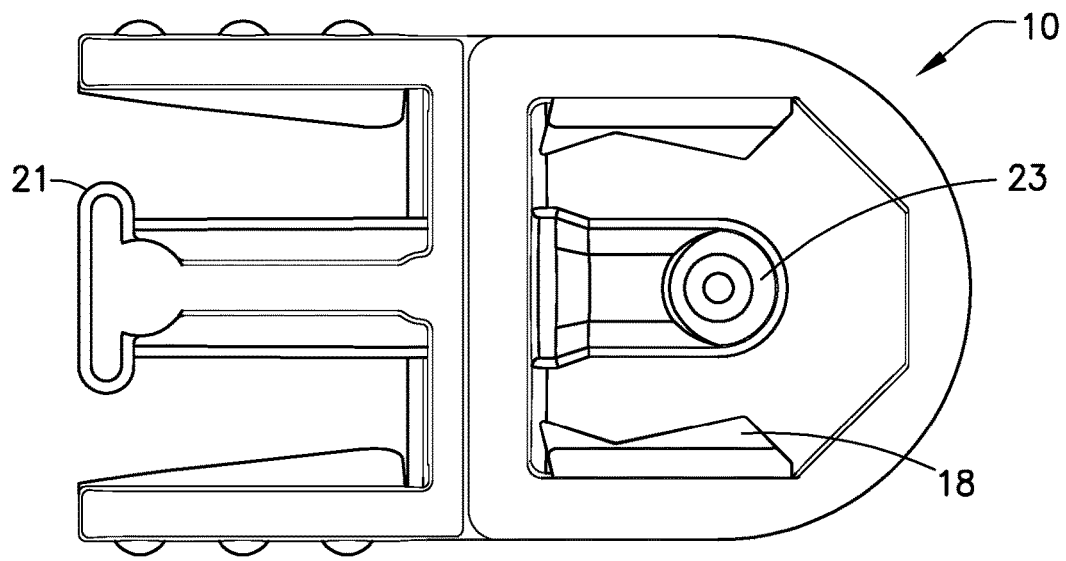
Figure 5:
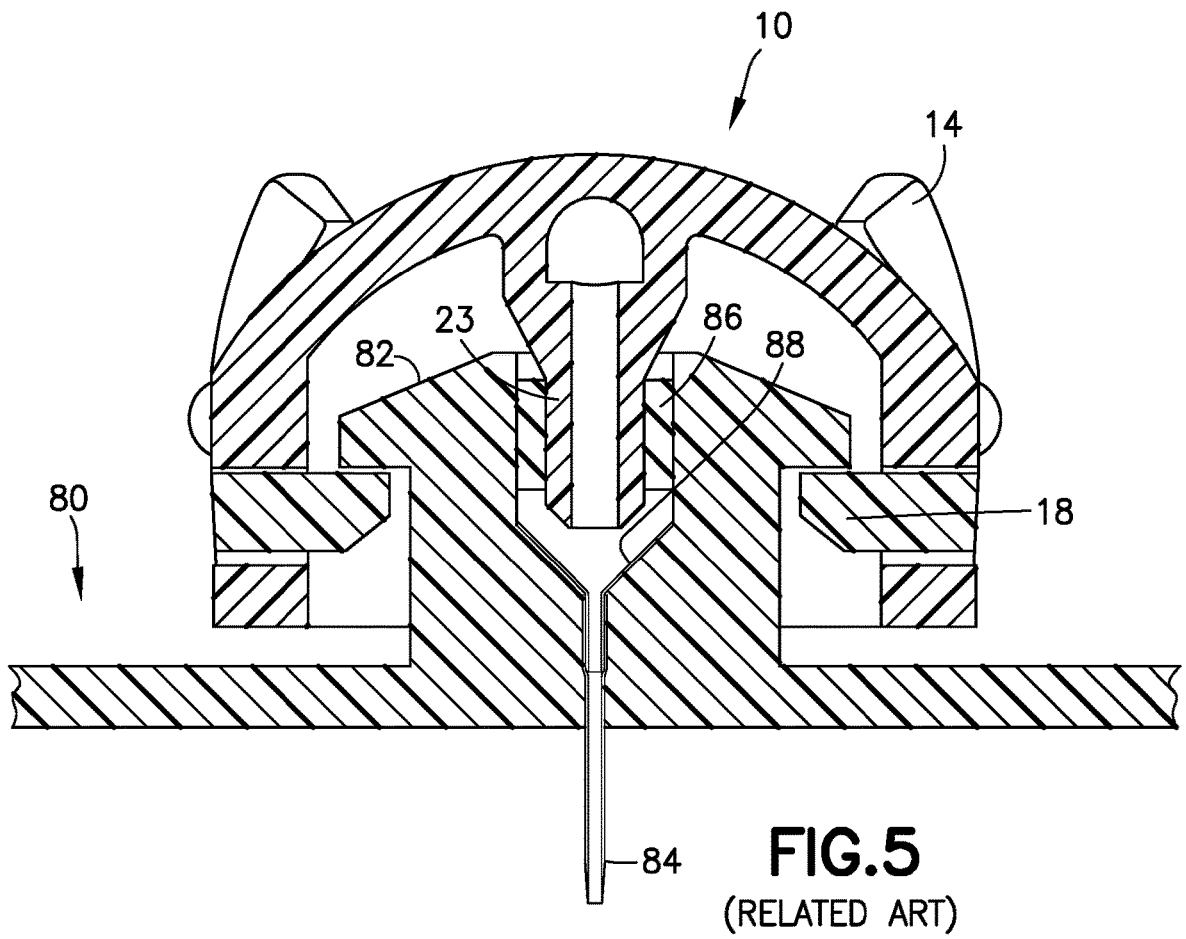

FIG. 3 is a perspective view of a related art two-piece fluid connector 10 and associated base 80, such as those found in PCT Publication WO 2013/086463, the disclosure of which is incorporated herein by reference for this purpose. FIG. 4 is a bottom view of the fluid connector 10, and FIG. 5 is a cross-sectional view of the fluid connector 10 connected with the base 80. The fluid connector 10 includes two components: a fluid path portion 12, and a latching portion 14. Together, the fluid path portion 12 and the latching portion 14 form a housing 15. The latching portion 14 includes activation levers 16, fluid connector latches 18, and a rigid stop 21.

The fluid path portion 12 includes a tubing connector portion 22 for connecting the fluid connector 10 with tubing 20. The fluid path portion 12 can be secured to the latching portion 14 via snap-fit engagement. As shown in FIG. 3, the tubing 20 is connected to a pump 14 via a connector 22. The pump 14 has a reservoir 6 for medicament to be delivered. The reservoir 6 is shown as being an internal reservoir, but one skilled in the art will understand that the reservoir 6 could be an external reservoir 6, such as a medicament vial, connected to the pump 14.

Figure 6:
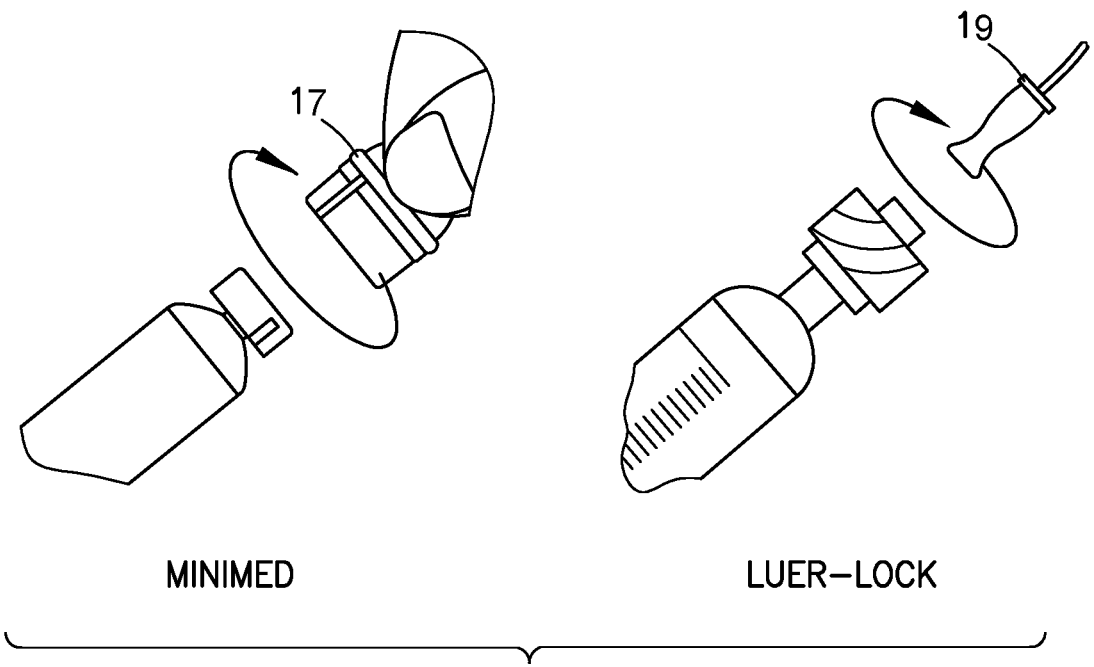
FIGS. 6-8 illustrate locations for pressure sensors in accordance with embodiments of the present invention.

As shown in FIGS. 4-6, the fluid path portion 12 has a blunt cannula 23 extending distally from a proximal interior surface of the housing 15. When connected to a corresponding base 80 with a patient cannula 84 that has been inserted into the user's skin, the blunt cannula 23 pierces a septum 86 in a mushroom-shaped head 82 of the base 80 to fluidly connect a pump with the patient cannula 84 on the distal side of the base 80. The patient cannula 84 is flexible, and is held in the base 80 by a metal wedge. Typically, the patient cannula 84 is inserted into a patient's skin using a known insertion device.

Figure 7:
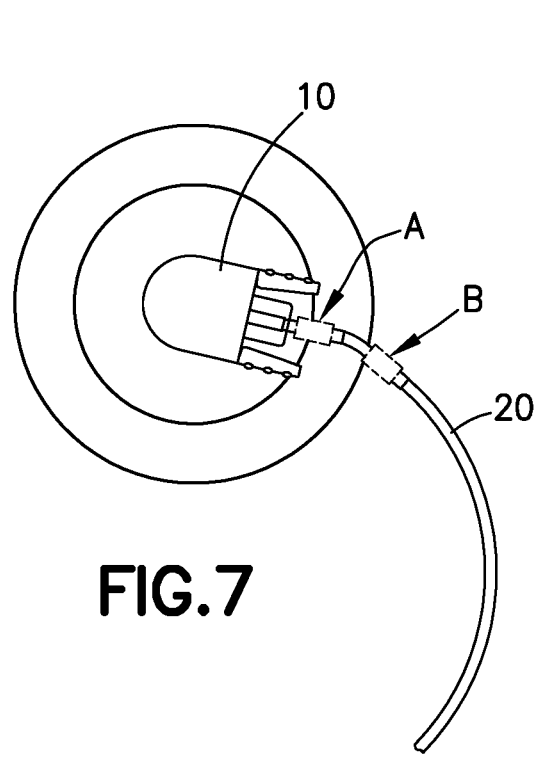
Figure 8:
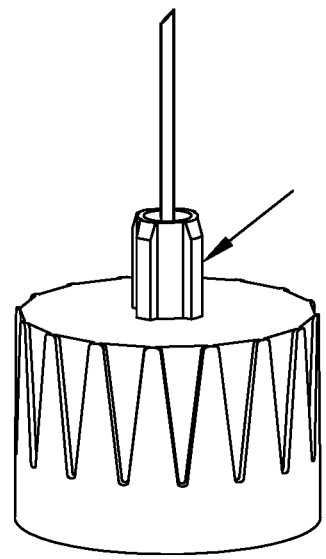
Figure 9:
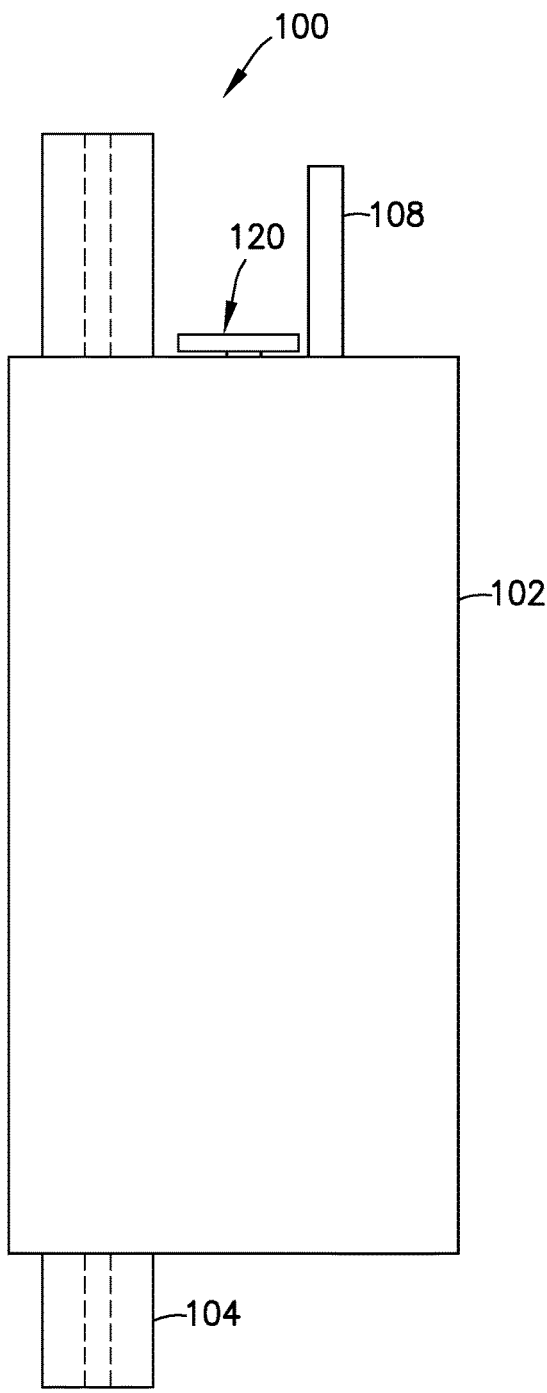
FIGS. 9-12 illustrate a pressure sensor in accordance with an embodiment of the present invention.

A pressure sensor in accordance with an embodiment of the present invention is external to a pressurizing system, such as a pump, and can be disposed in multiple locations. For example, the pressure sensor can be disposed within a connector 17 or 19 or 22 connecting an infusion line 20 to a pump 14 (FIGS. 3 and 6), in-line with the tubing 20 (FIG. 7), at the connect/disconnect site between the set 10 and the base 80 (e.g., position A) or in-line with the tubing (e.g., position B), or in the fluid path of a pen needle (FIG. 8) or a syringe, as subsequently described.

FIGS. 9-12 illustrate a pressure sensor 100 in accordance with an embodiment of the present invention. The pressure sensor 100 is disposed external to the pressurizing system (such as pump 14), and senses a back pressure in the fluid delivery path. The pressure sensor 100 provides an indication when the back pressure drops below a predetermined threshold after the pressurizing system ceases operation.

The pressure sensor 100 illustrated in FIGS. 9-12 includes a main body 102 with a primary fluid channel 104 therethrough. The primary fluid channel 104 is a portion of the fluid delivery path between the pressurizing system (e.g., pump 14) and the hollow cannula (e.g., patient cannula 84). Opposing ends of the primary fluid channel 104 fluidly connect to the infusion line set 10 and/or the tubing 20. For example, according to one embodiment, one end of the primary fluid channel 104 connects to the tubing 20, and the opposing end of the primary fluid channel 104 connects to the set or fluid connector 10 (e.g., position A of FIG. 7). According to another embodiment, both ends of the primary fluid channel connect to the tubing 20 (e.g., position B of FIG. 7).

Figure 10:
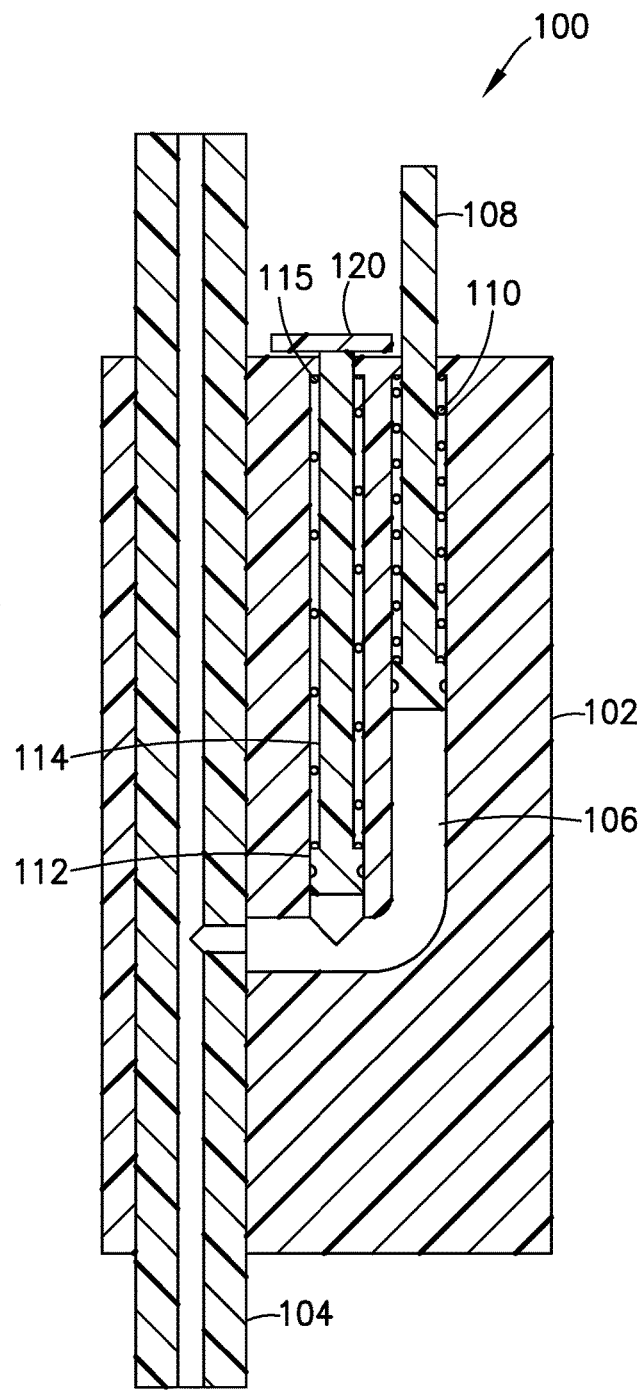
Figure 11:
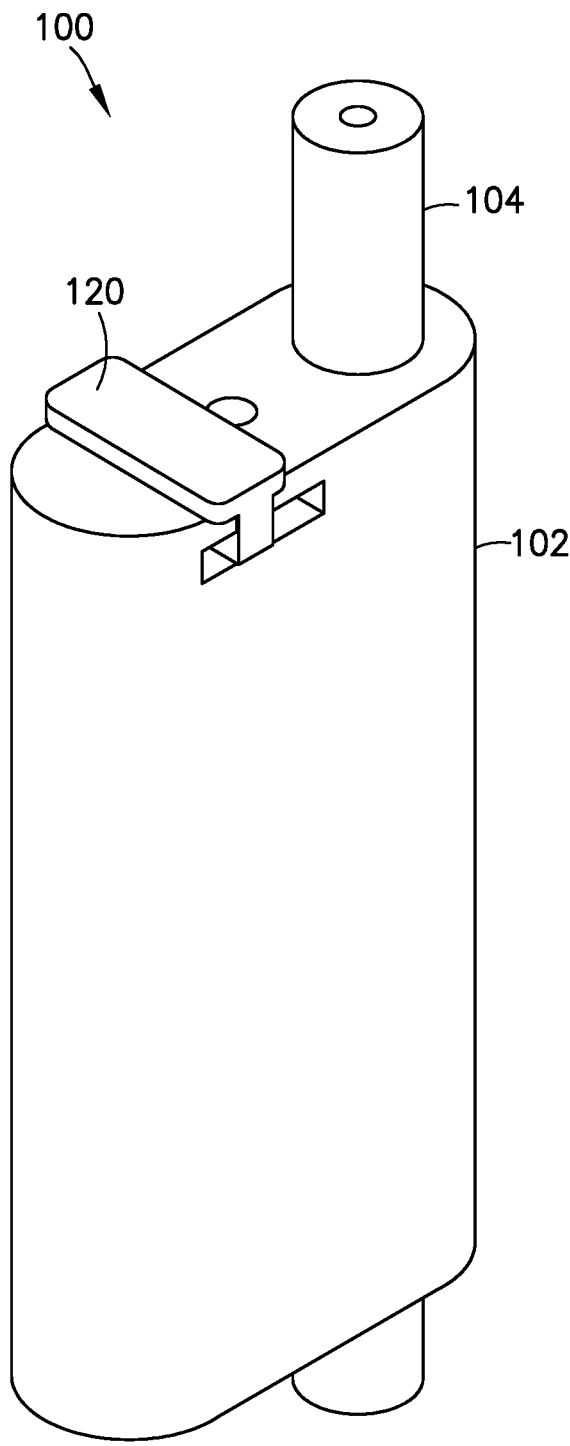
Figure 12:
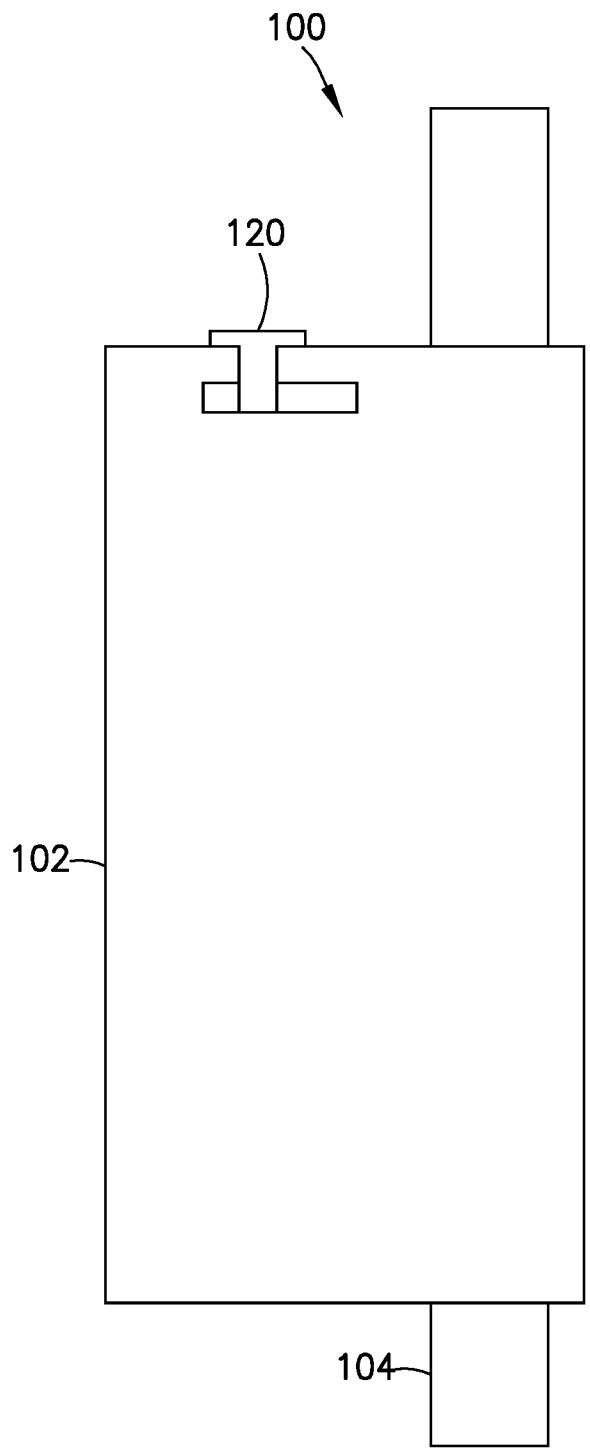

As best seen in FIG. 10, the pressure sensor 100 includes a gauge chamber 106 fluidly connected to the primary fluid channel 104, and a gauge 108 movably disposed within the gauge chamber 106. The gauge or first gauge 108 senses the back pressure in primary fluid channel 104, which is part of the fluid delivery path, and the gauge 108 extends outside the main body 102 when the back pressure exceeds the predetermined threshold. The gauge 108 withdraws into the main body 102 when the back pressure drops below the predetermined threshold after the pressurizing system (e.g., pump 14) ceases operation. According to one embodiment, the pressure sensor 100 includes a biasing member 110, such as a spring 110 biasing the gauge 108 inward with respect to the main body 102.

According to another embodiment, as shown in FIGS. 9-12, the pressure sensor 100 also includes a second gauge chamber 112 fluidly connected to the primary fluid channel 104, and a second gauge 114 movably disposed within the second gauge chamber 112, that senses the back pressure in the primary fluid channel 104, extends outside the main body 102 when the back pressure is greater than zero, and withdraws into the main body 102 when the back pressure is zero or less.

Preferably, the pressure sensor 100 also includes a second biasing member 115, such as a second spring 115 biasing the second gauge 114 inward with respect to the main body 102. According to one embodiment, the springs 110, 115 have different spring constants to accommodate different predetermined thresholds. For example, the spring 115 inwardly biasing the second gauge 114 inwardly can be weaker than the spring 110 inwardly biasing the first gauge 108. In such an embodiment, the second gauge 114 would extend from the main body 102 at a lower back pressure in the primary fluid channel 104 than what would be required to extend the first gauge 108.

In such an embodiment, when the first gauge 108 withdraws into the main body 102, the pressure sensor 100 the provides an indication to the user that it is safe to remove the fluid connector or set from the site or base 12 because the back pressure has dropped below the predetermined threshold after the pressurizing system (e.g., pump 14) ceases operation. According to one embodiment, the predetermined threshold is below about 0.5 psi. More preferably, the predetermined threshold is about 0.25 psi. Most preferably, the predetermined threshold is about 0.1 psi.

Figure 13:
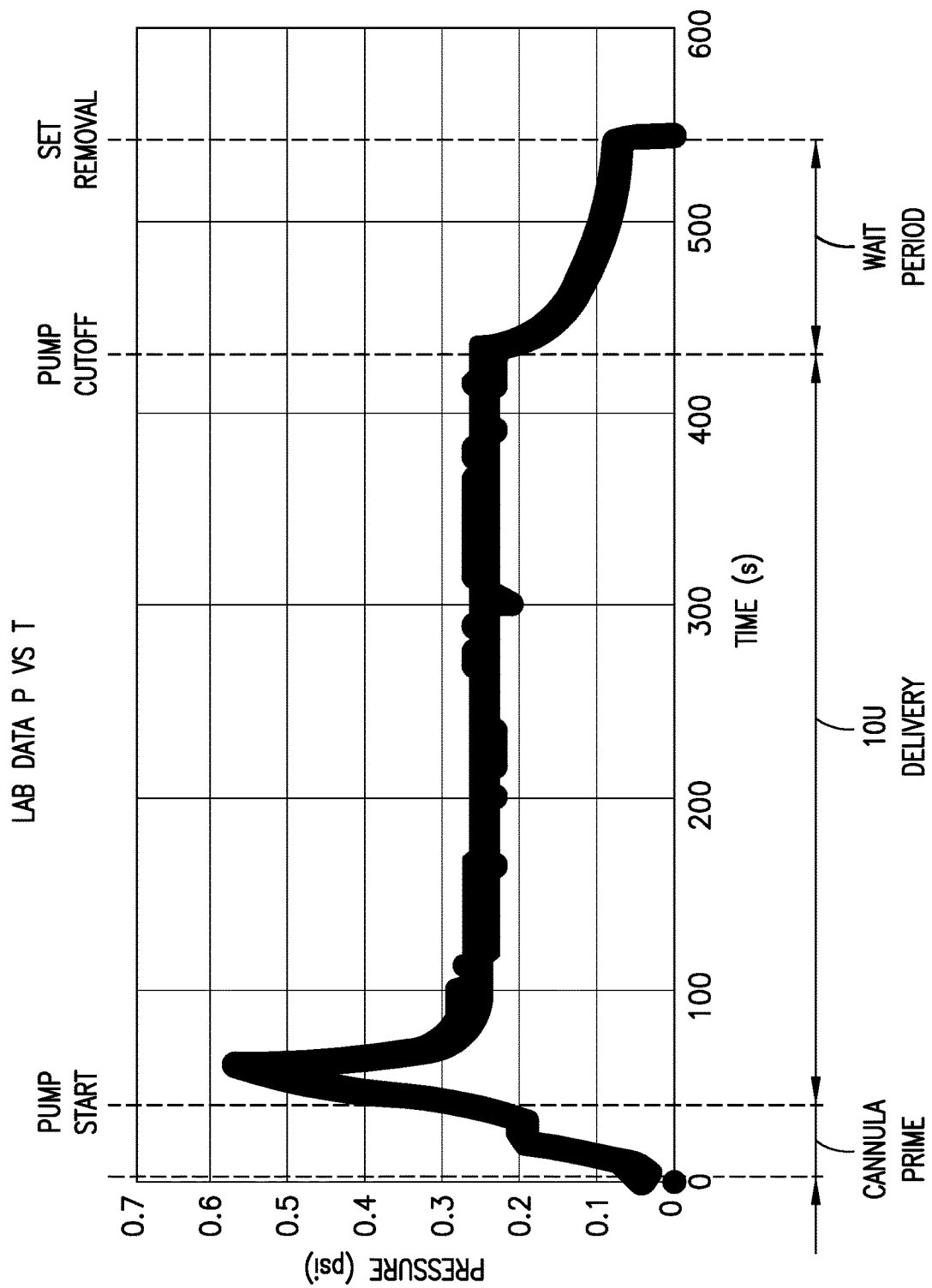
FIGS. 13 and 14 are graphs illustrating pressure versus time conditions of medicament delivery devices.

As shown in FIG. 13, with one combination of pump, tubing, fluid connector, and base, during operation of the pump, after an initial spike, the pump provides 0.28 psi during delivery, and the pressure tapers off after the pump cuts off. During the wait period after the pump cuts off, there is still the potential for medicament delivery, and thus, for such a combination, the predetermined threshold would preferably be about 0.1 psi, to indicate that the intended dosage has been received and it is safe to remove the fluid connector from the base.

Figure 14:
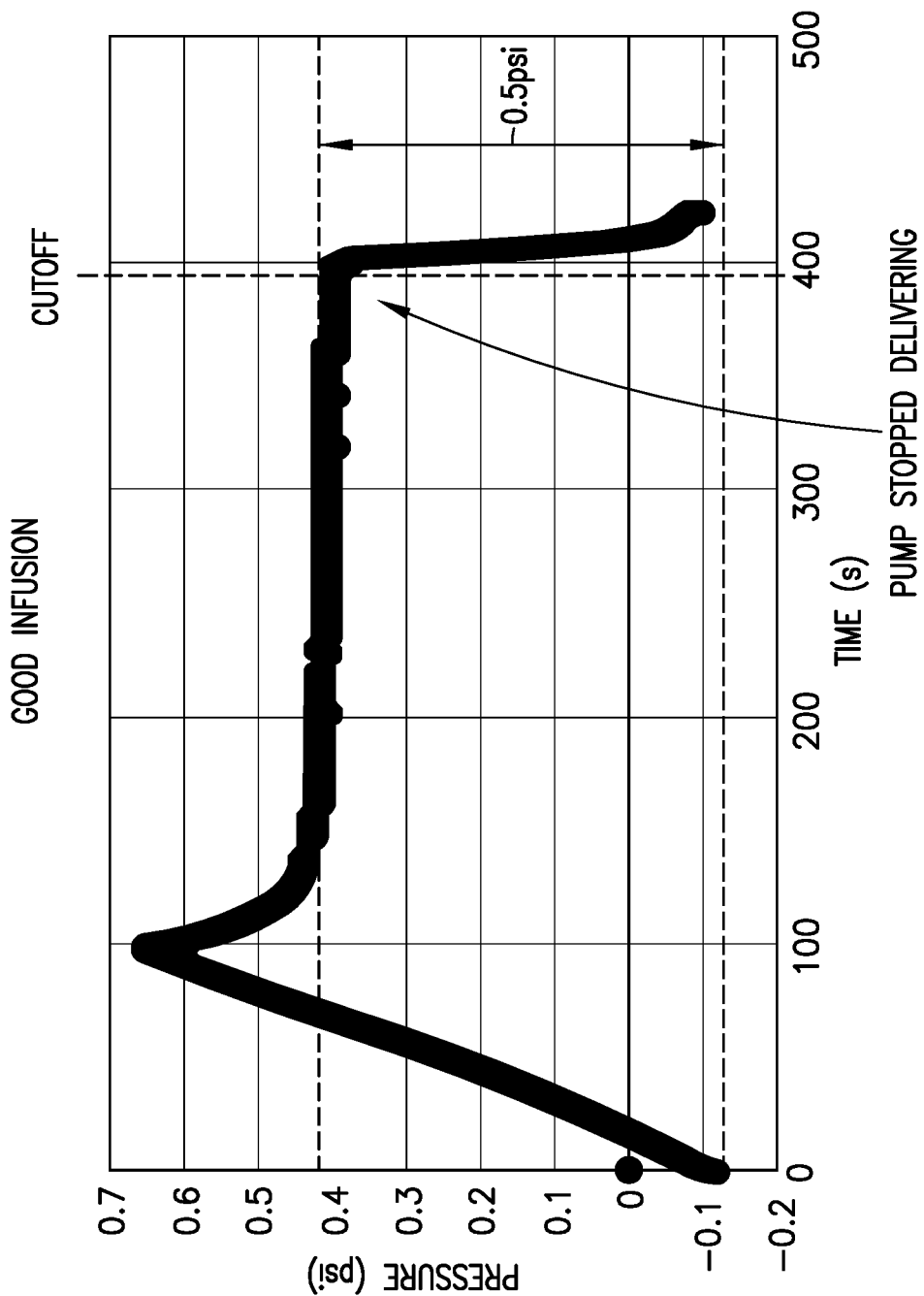

As shown in FIG. 14, with another combination of pump, tubing, fluid connector, and base, during operation of the pump, the pump provides about 0.4 psi prior to cutoff. For such a combination, the predetermined threshold would preferably be about 0.1-0.2 psi, to indicate that the intended dosage has been received and it is safe to remove the fluid connector from the base.

In the embodiment shown in FIGS. 9-12, when the second gauge 108 is withdrawn into the main body 102 and the pump is operating, the pressure sensor 100 provides an indication to the user that the insertion of the base into the skin or the connection of the fluid connector to the base is faulty because there is no back pressure in the primary fluid channel 104. In other words, if the cannula of the base were not inserted in the patient's skin, or if the fluid connector were not connected to the base, when the pump was operating, the fluid would flow through the fluid delivery path without any resistance (other than the inherent resistance of, for example, the tubing), and thus, there would be little or no back pressure in the primary fluid channel 104.

When the pump is operating and the second gauge 108 extends from the main body 102, the pressure sensor 100 provides an indication to the user that the base is sufficiently inserted and the connection between the fluid connector and the base is satisfactory, because the back pressure in the primary fluid channel 104 is greater than zero.

According to one embodiment, the pressure sensor 100 includes a sliding cap 120 (best shown in FIGS. 11 and 12) to selectively cover either the gauge 108 or the second gauge 114 so that only an uncovered one of the gauges 108 and 114 is operational at a given time. For example, during insertion of the base into the user's skin and the initial operation of the pump, the user may have the sliding cap covering the first gauge 108, so that the second gauge 114 can provide an indication that the insertion is successful. Subsequently, once the user is assured of successful insertion and connection, the user can slide the sliding cap 120 to cover the second gauge 114, and thus monitor the condition of the first gauge 108 to determine when it is safe to remove the fluid connector 10 from the base 80 to ensure proper dosage delivery.

According to one embodiment, the user needs to depress the second gauge 114 to slide the sliding cap 120 over the second gauge 114. According to another embodiment, the sliding cap has a ramp that engages a corresponding ramp on the second gauge 114 so that the act of sliding the sliding cap 120 over the second gauge 114 depresses the second gauge 114 to enable the sliding cap 120 to cover the second gauge 114.

According to one embodiment, the sliding cap 120 can be positioned not to cover either of the gauges 108 and 114, and both gauges 108 and 114 are able to extend from the main body 102 at the same time. According to another embodiment, there is no sliding cap, and both gauges 108 and 114 are able to extend from the main body 102 at the same time.

Figure 15:
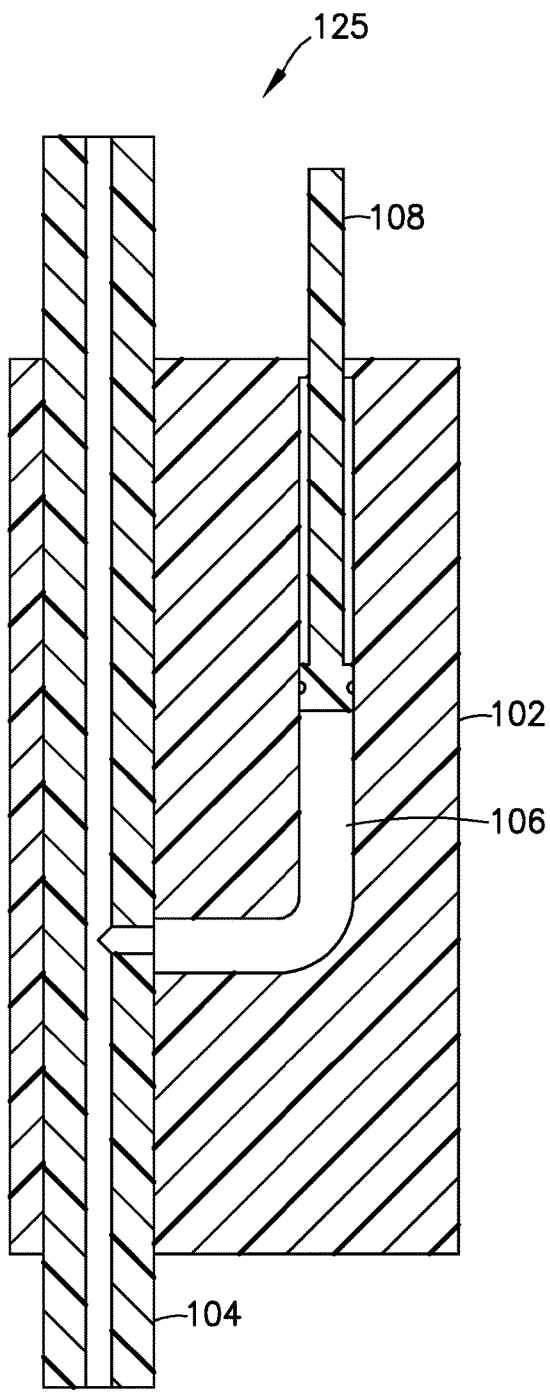
FIG. 15 illustrates a pressure sensor in accordance with another embodiment of the present invention.

According to another embodiment shown in FIG. 15, the pressure sensor 125 only includes a single gauge chamber 106 and the single gauge 108. In addition, the pressure sensor 125 does not include a biasing member or spring. According to one embodiment, the pressure sensor 125 should be kept upright during operation, and the weight of the gauge 108 retracts the gauge 108 within the main body 102 when the back pressure has dropped below the predetermined threshold after the pressurizing system (e.g., pump 14) ceases operation, thereby signifying proper dosage delivery and that it is safe to remove the fluid connector 10 from the base 80. In other respects, the pressure sensor 125 operates similarly to pressure sensor 100, and further description thereof is omitted for brevity.

Figure 16:
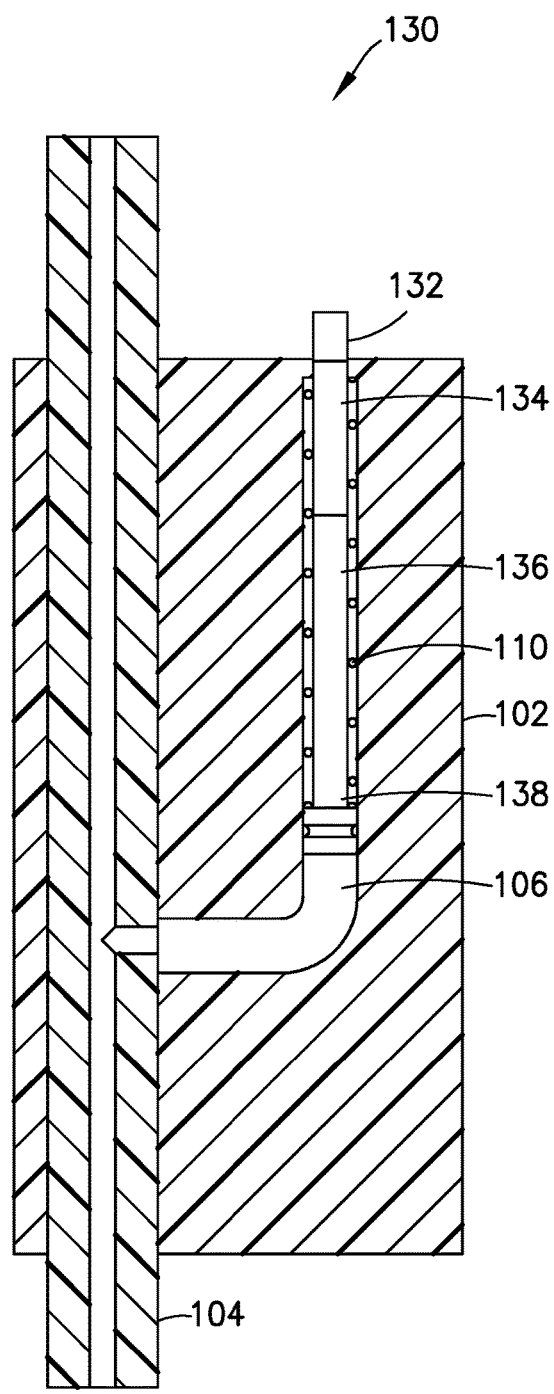
FIG. 16-18 illustrate a pressure sensor in accordance with another embodiment of the present invention.
Figure 17:
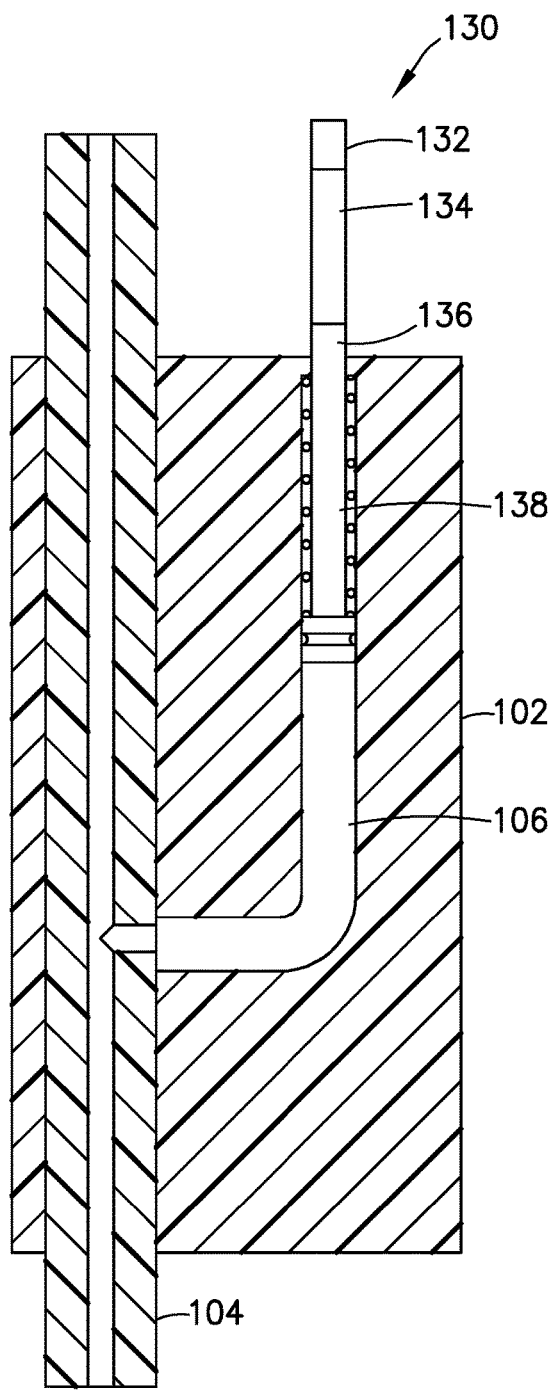
Figure 18:
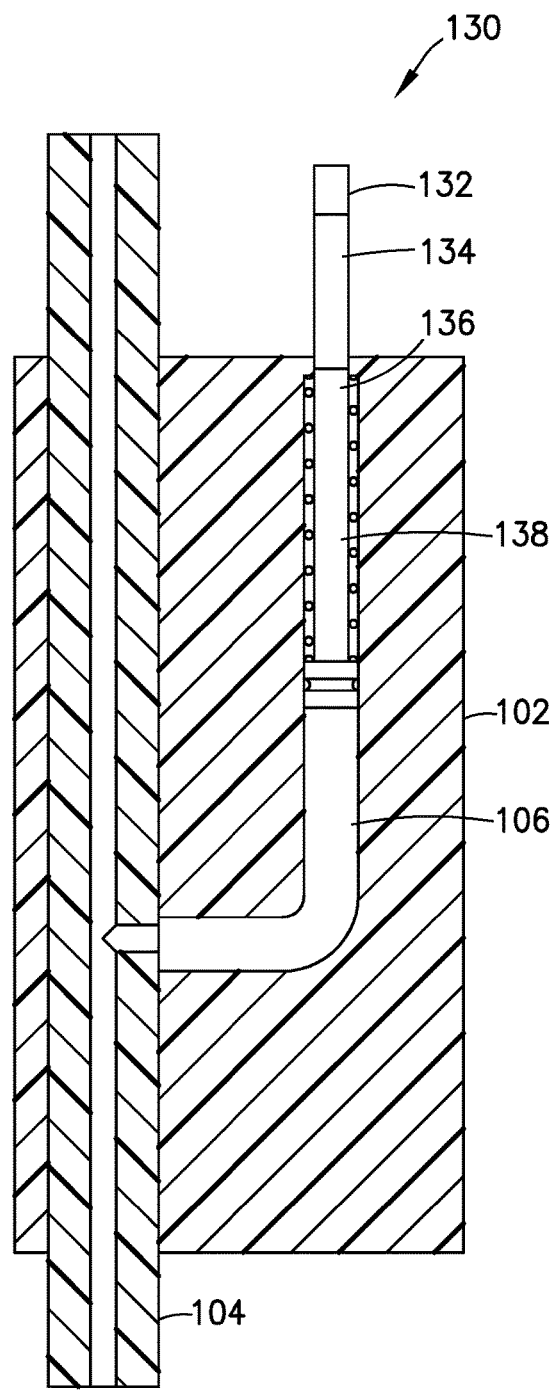

According to another embodiment shown in FIGS. 16-18, the pressure sensor 130 also only includes a single gauge chamber 106 and a single gauge 138, but includes the functionality of the two gauges of pressure sensor 100 of FIGS. 9-12. More specifically, in this embodiment, the gauge 108 has three bands 132, 134, and 136 of demarcation, for example, texture or color.

Like the second gauge 114 of previously describe pressure sensor 100, against the bias of spring 110, the gauge 138 extends a first distance from the main body 102 when the back pressure is greater than zero, and withdraws into the main body 102 when the back pressure is zero or less. When the gauge extends this first distance, as shown in FIG. 16, only the first band 132 is visible outside of the main body 102.

Figure 19:
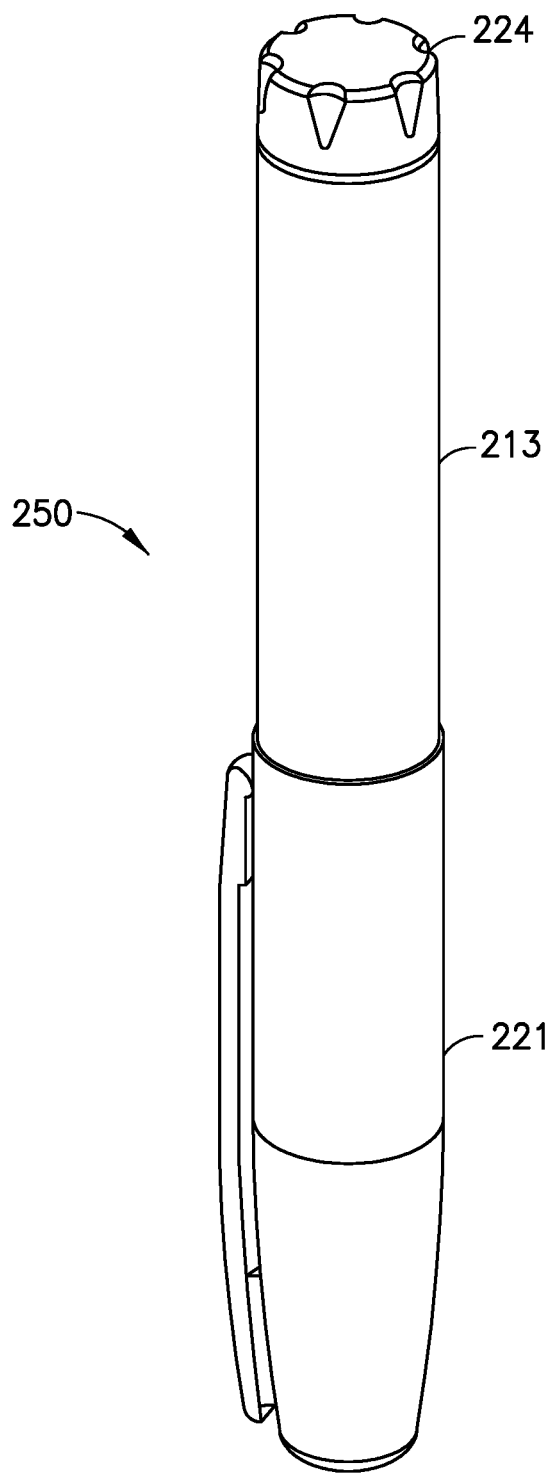
FIG. 19 illustrates a medicament delivery pen.
Figure 20:
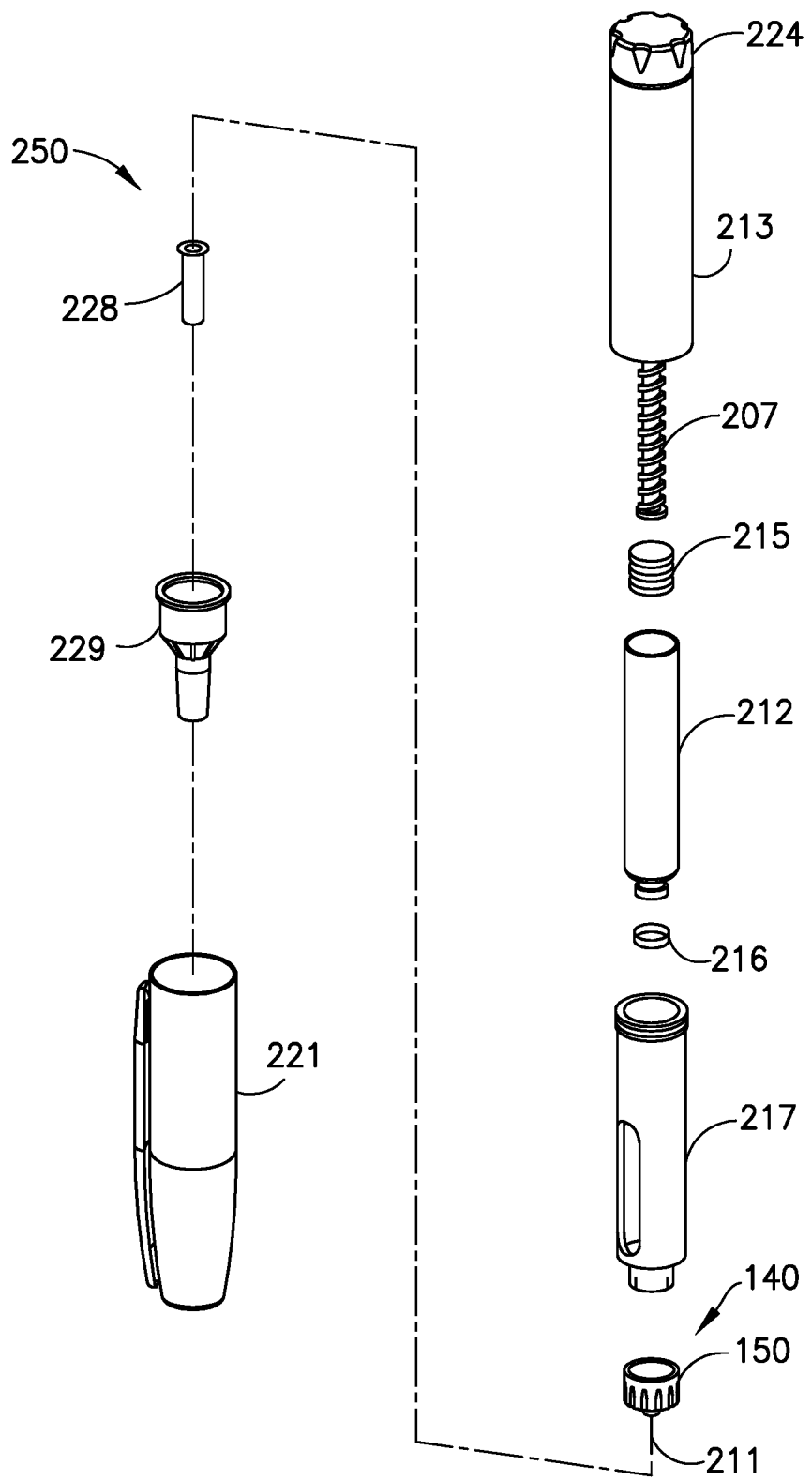
FIG. 20 is an exploded view of the medicament delivery pen of FIG. 19 with another embodiment of the present invention.

When the back pressure meets or exceeds the predetermined threshold, the gauge 138 extends outside of the main body 102 by a second distance, and all three bands 132, 134, and 136 are visible outside the main body 102 (FIG. 17). And when the back pressure in the gauge chamber 106 is less than the predetermined pressure but greater than the first, non-zero pressure, the gauge 138 extends from the main body 102 by a third distance when the back pressure drops below the predetermined threshold after the pressurizing system ceases operation and only the first and second bands 132 and 134 are visible outside of the main body 102, as shown in FIG. 18. Pen injection devices, such as an exemplary pen injector 250, as shown in FIGS. 19 and 20, typically comprise a dose knob/button 224, an outer sleeve 213, and a cap 221. The dose knob/button 224 allows a user to set the dosage of medication to be injected. The outer sleeve 213 is gripped by the user when injecting medication. The cap 221 is employed by the user to securely hold the pen injector 250 in a shirt pocket, purse, or other suitable location.

FIG. 20 is an exploded view of the exemplary medicament delivery pen 250 shown in FIG. 19. The dose knob/button 24 has a dual purpose and is used to both set the dosage of the medication to be injected and to inject the dosed medicament via a lead screw 207 and stopper 215 from a medicament cartridge 212, which is attached to the drug delivery pen through a lower housing 217. The medicament cartridge 212 is typically a glass tube sealed at one end with a septum 216 and at the other end with the stopper 215. In standard drug delivery pens, the dosing and delivery mechanisms are all found within the outer sleeve 213. Those mechanisms are not described in greater detail herein as they are understood by those skilled in the art. According to one embodiment of the present invention, pressure sensor 140 includes pen needle hub 150

Figure 22:
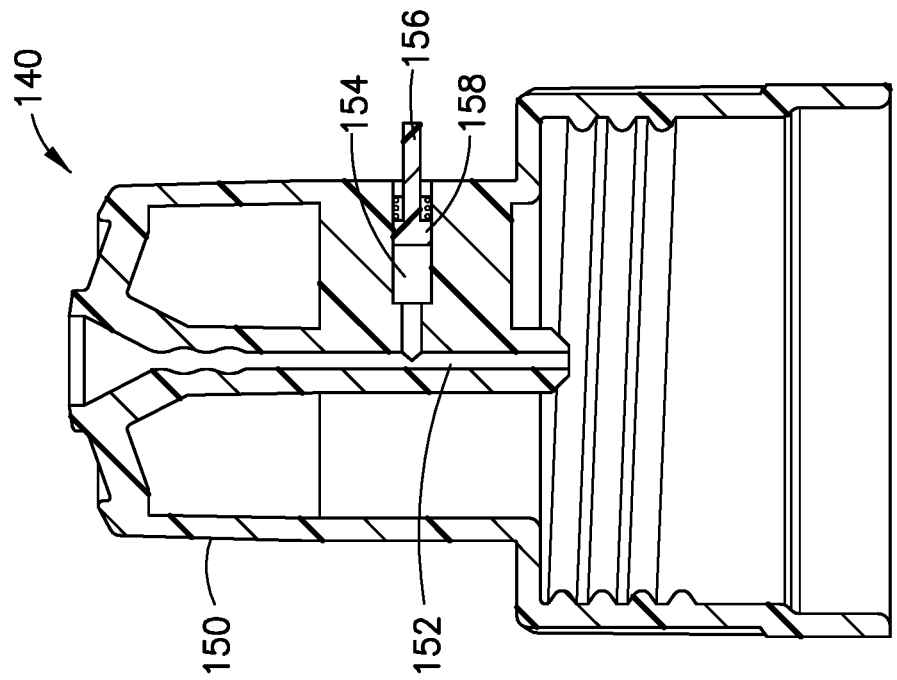
FIGS. 21 and 22 illustrate a pressure sensor in accordance with another embodiment of the present invention.
Figure 21:
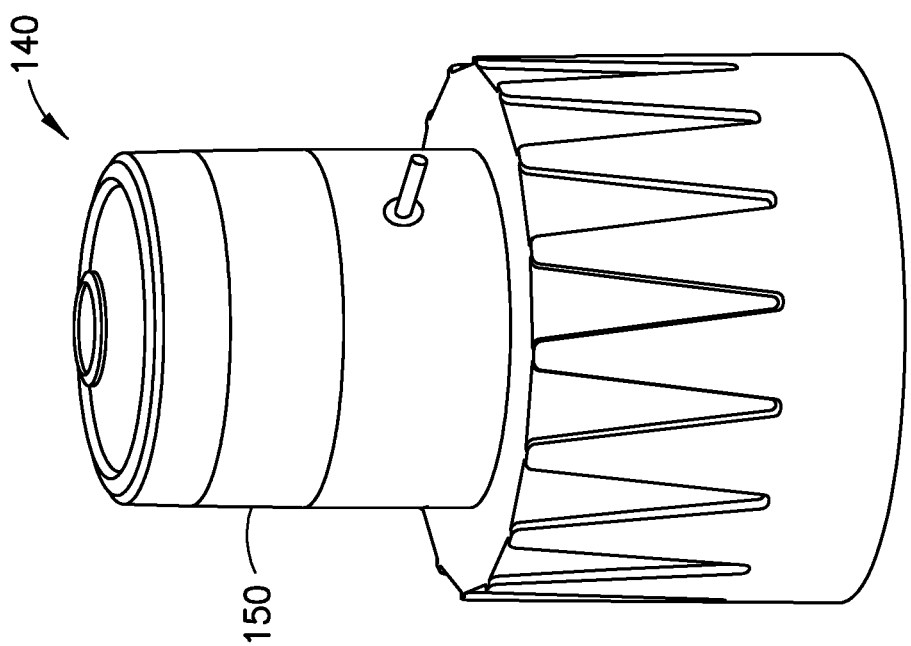

FIGS. 21 and 22 illustrate the pressure sensor 140 in greater detail, with the needle 211 omitted for clarity. Pressure sensor 140 has a primary fluid channel 152 therethrough, a gauge chamber 154, and a gauge 156 movably disposed in the gauge chamber 154. Preferably, the pressure sensor 140 also includes a biasing member 158 inwardly biasing the gauge 156 with respect to the hub 150. According to one embodiment, the needle 211 has a sharpened distal patient end for insertion into a patient, and a sharpened proximal end for penetrating a septum of, for example, cartridge 212. The two ends of the needle 211 are in fluid communication with each other. In such an embodiment, the needle 211 has a lateral opening communicating with the gauge chamber 154. According to another embodiment, the needle 211 only has a sharpened distal patient end, which communicates with a fluid path (e.g., primary fluid channel 152) that communicates with the cartridge 212, for example, via a spike. In such an embodiment, the gauge chamber fluidly communicates with the fluid path.

Operation of the pressure sensor 140 is substantially similar to the operation of the pressure sensor 100, 125 or 130, and is therefore omitted for brevity. Similar to the pressure sensor 100, in other embodiments, the pressure sensor 140 can also include a second gauge chamber, a second gauge, a second biasing member, and a sliding cap, but preferably does not, because a user can usually see whether a pen needle has been successfully inserted.

Figure 23:
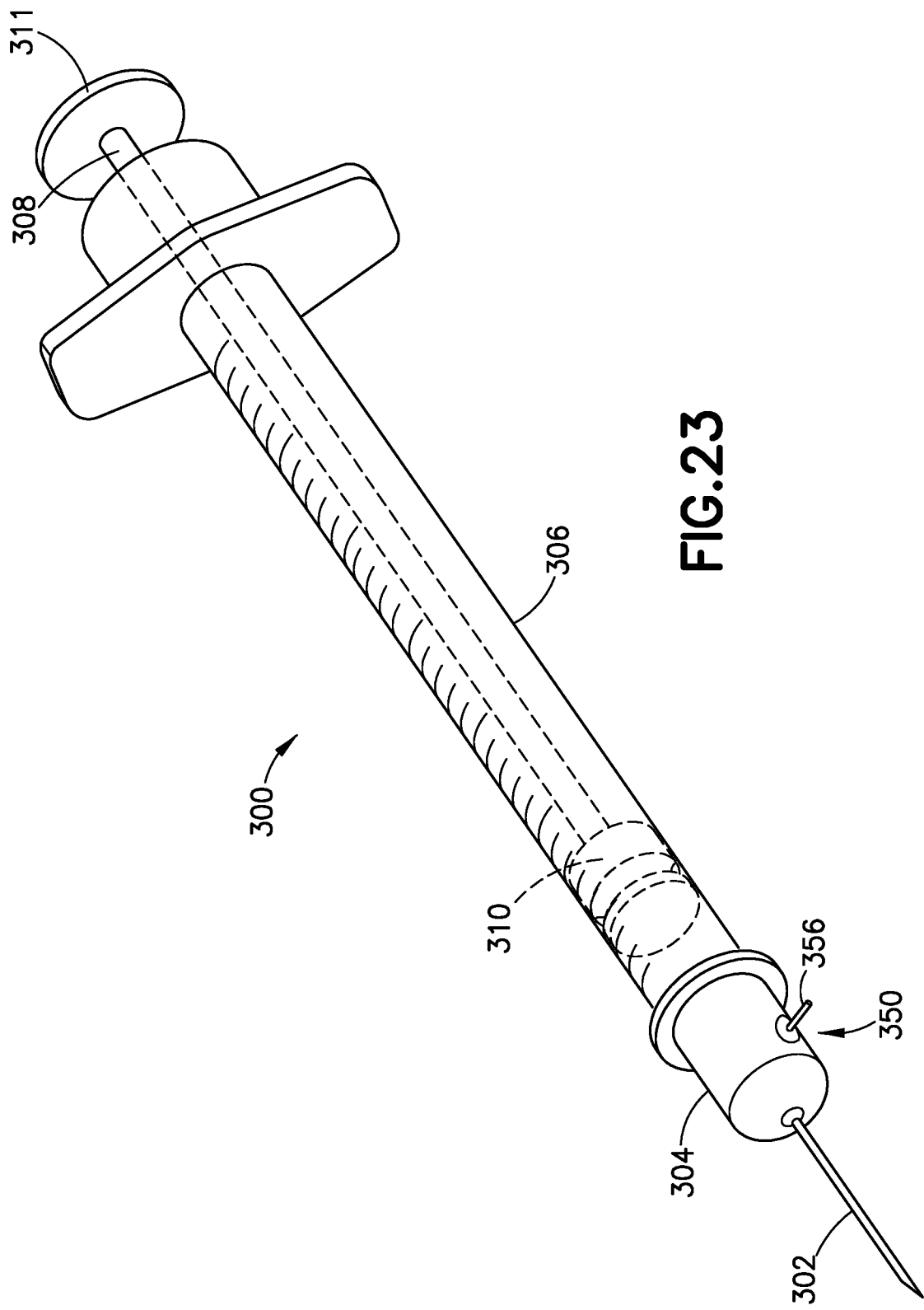
FIG. 23 illustrates a medicament delivery syringe with a pressure sensor in accordance with another embodiment of the present invention.
Figure 24:
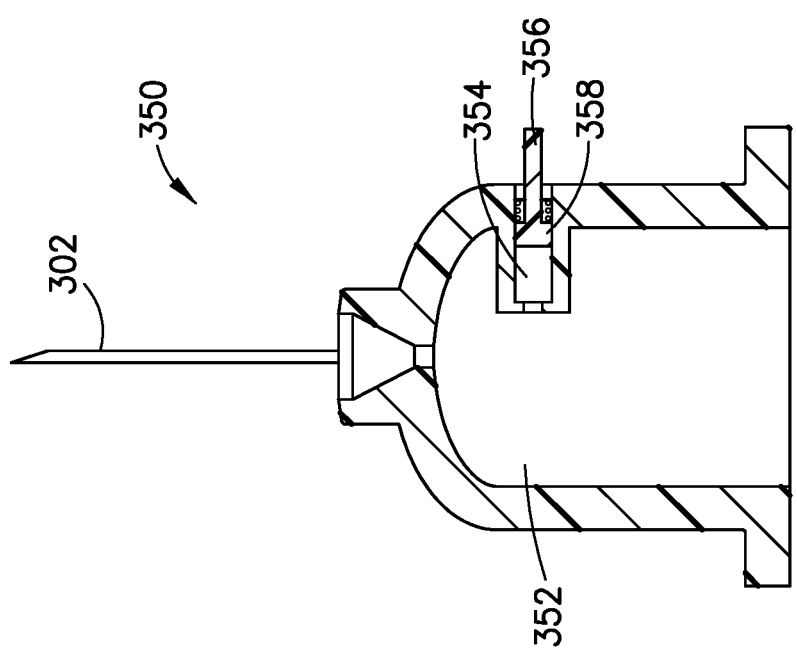
FIG. 24 is a cross-sectional view of a needle and needle hub of the syringe of FIG. 23.

FIG. 23 illustrates an exemplary embodiment of a medication delivery device such as a plastic disposable syringe 300 having a needle 302 at its proximal end and disposed in a molded needle hub 304 that includes a pressure sensor 350. FIG. 24 is a cross-sectional view of the needle 302, the needle hub 304, and the pressure sensor 350. The needle hub 304 is fastened to an open proximal end of a molded cylindrical barrel 306, and a plunger 308 is disposed at an open distal end of the cylindrical barrel 306. The plunger 308 includes a stopper 110 that is configured to seal the distal end of the barrel 306. The stopper 310 may be integral to the plunger 108. A distal end of the plunger 308 includes a thumb press 311 to provide an interface for a user to move the plunger 308 in the axial direction of the barrel 106. By pulling or depressing the plunger, a user is able to transfer fluids to and from the syringe 300 at its proximal end via the needle 302.

Pressure sensor 350 has a primary fluid channel 352 therethrough, a gauge chamber 354, and a gauge 356 movably disposed in the gauge chamber 354. Preferably, the pressure sensor 350 also includes a biasing member 358 inwardly biasing the gauge 356 with respect to the hub 304.

Operation of the pressure sensor 350 is substantially similar to the operation of the pressure sensor 100, 125, 130, or 140, and is therefore omitted for brevity. Similar to the pressure sensor 100, in other embodiments, the pressure sensor 350 can also include a second gauge chamber, a second gauge, a second biasing member, and a sliding cap, but preferably does not, because a user can usually see whether a needle 302 has been successfully inserted.

Figure 25:
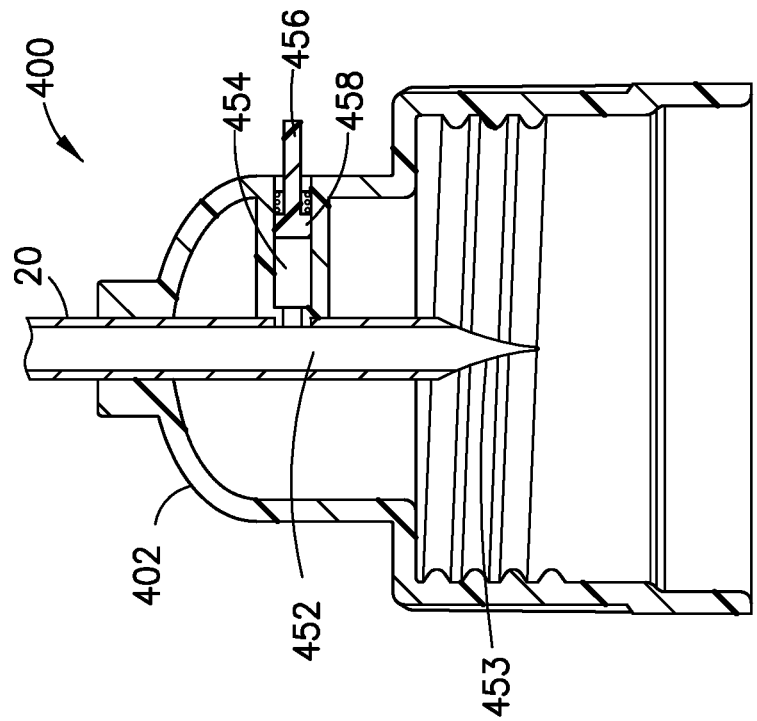
FIG. 25 illustrates a pressure sensor in accordance with another embodiment of the present invention.

A connector 402 for connecting tubing 20 to a pump (e.g., pump 14) is illustrated in FIG. 25, and includes a pressure sensor 400 in accordance with another embodiment of the present invention. The pressure sensor 400 has a primary fluid channel 452 therethrough, including a spike 453 for penetrating a septum of the pump 14 or a reservoir. The pressure sensor 400 also includes a gauge chamber 454 and a gauge 456 movably disposed in the gauge chamber 454. Preferably, the pressure sensor 400 also includes a biasing member 458 inwardly biasing the gauge 456 with respect to the connector 402.

Operation of the pressure sensor 400 is substantially similar to the operation of the pressure sensor 100, 125, 130, 140, or 350, and is therefore omitted for brevity. Similar to the pressure sensor 100, in other embodiments, the pressure sensor 400 can also include a second gauge chamber, a second gauge, a second biasing member, and a sliding cap.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

Various aspects of the multiple embodiments may be employed independently or in combinations thereof.

What is claimed is:
1. A medicament delivery pen comprising:
a reservoir for holding a medicament;
a pressurizing system that dispenses the medicament from the reservoir when operating;
a needle hub housing a hollow cannula, the hollow cannula having a distal end for insertion into a patient;
a fluid delivery path disposed between the pressurizing system and the distal end of the hollow cannula and communicating the medicament therebetween; and
a pressure sensor external to the pressurizing system and disposed in the hub, sensing a back pressure in the fluid delivery path, and providing an indication when the back pressure drops below a predetermined threshold after the pressurizing system ceases operation;
wherein the hub comprises a primary fluid channel therethrough, the primary fluid channel being a portion of the fluid delivery path and being connected with the distal end of the hollow cannula; and
the pressure sensor comprises:
a gauge chamber fluidly connected to the primary fluid channel;
a gauge movably disposed within the gauge chamber, sensing the back pressure in the fluid delivery path, extending outside the hub when the back pressure exceeds the predetermined threshold, and withdraw- ing into the hub when the back pressure drops below the predetermined threshold after the pressurizing system ceases operation;

a second gauge chamber fluidly connected to the primary fluid channel; and a second gauge movably disposed within the second gauge chamber, sensing the back pressure in the fluid delivery path, extending outside the hub when the back pressure is greater than zero, and withdrawing into the hub when the back pressure is zero or less.

2. The medicament delivery pen according to claim 1, wherein the pressure sensor further comprises a biasing member biasing the gauge inward with respect to the hub.

3. The medicament delivery pen according to claim 1, wherein the pressure sensor further comprises: a biasing member biasing the gauge inward with respect to the hub; and a second biasing member biasing the second gauge inward with respect to the hub.

4. A medicament delivery syringe, comprising:

a reservoir for holding a medicament;

a pressurizing system that dispenses the medicament from the reservoir when operating;

a needle hub housing a hollow cannula, the hollow cannula having a distal end for insertion into a patient;

a fluid delivery path disposed between the pressurizing system and the distal end of the hollow cannula and communicating the medicament therebetween; and a pressure sensor external to the pressurizing system and disposed in the hub, sensing a back pressure in the fluid delivery path, and providing an indication when the back pressure drops below a predetermined threshold after the pressurizing system ceases operation;

wherein the hub comprises a primary fluid channel therethrough, the primary fluid channel being a portion of the fluid delivery path and being connected with the hollow cannula; and the pressure sensor comprises:

a gauge chamber fluidly connected to the primary fluid channel;

a gauge movably disposed within the gauge chamber, sensing the back pressure in the fluid delivery path, extending outside the hub when the back pressure exceeds the predetermined threshold, and withdrawing into the hub when the back pressure drops below the predetermined threshold after the pressurizing system ceases operation;

a second gauge chamber fluidly connected to the primary fluid channel; and a second gauge movably disposed within the second gauge chamber sensing the back pressure in the fluid delivery path, extending outside the hub when the back pressure is greater than zero, and withdrawing into the hub when the back pressure is zero or less.

5. The medicament delivery syringe according to claim 4, wherein the pressure sensor further comprises a biasing member biasing the gauge inward with respect to the hub.

6. The medicament delivery syringe according to claim 4, wherein the pressure sensor further comprises: a biasing member biasing the gauge inward with respect to the hub; and a second biasing member biasing the second gauge inward with respect to the hub.

* * * * *